(12) United States Patent
Morita

(10) Patent No.: US 9,452,979 B2
(45) Date of Patent: Sep. 27, 2016

(54) METHOD FOR SYNTHESIZING ORGANIC MATTER AND SUBMERGED PLASMA DEVICE

(71) Applicant: PM DIMENSIONS KABUSHIKI KAISHA, Kyoto (JP)

(72) Inventor: Tatsuo Morita, Kyoto (JP)

(73) Assignee: PM DIMENSIONS KABUSHIKI KAISHA, Kyoto (JP)

( * ) Notice: Subject to any disclaimer, the term of this patent is extended or adjusted under 35 U.S.C. 154(b) by 0 days.

(21) Appl. No.: 14/917,842

(22) PCT Filed: Sep. 9, 2014

(86) PCT No.: PCT/JP2014/073730
§ 371 (c)(1),
(2) Date: Mar. 9, 2016

(87) PCT Pub. No.: WO2015/037565
PCT Pub. Date: Mar. 19, 2015

(65) Prior Publication Data
US 2016/0221942 A1    Aug. 4, 2016

(30) Foreign Application Priority Data
Sep. 10, 2013  (JP) .................................. 2013-187574

(51) Int. Cl.
*H05F 3/00* (2006.01)
*C07C 407/00* (2006.01)
(Continued)

(52) U.S. Cl.
CPC ............ *C07C 407/00* (2013.01); *B01J 19/088* (2013.01); *H05H 1/2406* (2013.01); *B01J 2219/0809* (2013.01); *B01J 2219/0869* (2013.01);
(Continued)

(58) Field of Classification Search
CPC . C07C 407/00; C07C 409/24; C07C 409/34; B01J 19/088; B01J 2219/0809; B01J 2219/0869; B01J 2219/0884; B01J 2219/0815; B01J 2219/0835; B01J 2219/0841; B01J 2219/0849; B01J 2219/0877; H05H 1/2406; H05H 2001/2412; Y02W 10/37; C02F 1/46
See application file for complete search history.

(56) References Cited

U.S. PATENT DOCUMENTS 6,376,977 B1    4/2002   Kawai et al.
2009/0194408 A1 8/2009   Yang et al.

FOREIGN PATENT DOCUMENTS

JP    05-117183    *  5/1993
JP    2000-349073 A   12/2000
(Continued)

OTHER PUBLICATIONS

Sano et al, "Decomposition of organic compounds in water by direct contact of gas corona discharge: influence of discharge conditions", Ind. Eng. Chem. Res., 2002, 41, p. 5906-5911.*

(Continued)

*Primary Examiner* — Xiuyu Tai
(74) *Attorney, Agent, or Firm* — Renner, Otto, Boisselle & Sklar, LLP

(57) ABSTRACT

An organic substance synthesis method according to an embodiment of the present invention is carried out using a submerged plasma device (1000), for example, and the method includes: forming a plasma through discharge in a gas including a carbon dioxide as in contact with water; and generating an organic substance including performic acid or diformyl peroxide in the water by contact between the plasma and the water.

4 Claims, 20 Drawing Sheets

(51) Int. Cl.
*B01J 19/08* (2006.01)
*H05H 1/24* (2006.01)

(52) U.S. Cl.
CPC .............. *B01J2219/0884* (2013.01); *H05H 2001/2412* (2013.01)

(56) References Cited

FOREIGN PATENT DOCUMENTS

| JP | 2004-268003 A | 9/2004 |
|---|---|---|
| JP | 2008-178870 A | 8/2008 |
| JP | 2009-114001 A | 5/2009 |
| JP | 2009-202154 A | 9/2009 |
| JP | 2010-137212 A | 6/2010 |
| JP | 2013-049015 A | 3/2013 |

OTHER PUBLICATIONS

International Search Report for corresponding International Application No. PCT/JP2014/073730 mailed Dec. 16, 2014.
Malik; "Water Purification by Plasmas: Which Reactors are Most Energy Efficient?", Plasma Chem. Plasma Process (2010) 30:21-31; DOI 10.1007/s11090-009-9202-2.
Yasuoka et al., "Generation of Underwater Discharge Plasma and its Property", J. Plasma Fusion Res. vol. 84, No. 10 (2008) pp. 666-673 and concise English translation.
Alexander Fridman, "Plasma Chemistry", Cambridge University Press 2008; IBSN-13 978-0-511-39857-5.
Kawasaki et al., "Facile Carbon Fixation to Performic Acids by Water-Sealed Dielectric Barrier Discharge", Scientific Reports, Oct. 6, 2015, 5:14737; DOI 10.1038/srep14737.

* cited by examiner (a)

(b)

(a)

(b)

(a)

(b)

METHOD FOR SYNTHESIZING ORGANIC MATTER AND SUBMERGED PLASMA DEVICE

TECHNICAL FIELD

The present invention relates to an organic substance synthesis method and a treatment method using a submerged plasma, and also to a submerged plasma device for use with these methods.

BACKGROUND ART

A submerged plasma is a non-equilibrium plasma in contact with a liquid. A submerged plasma is formed by causing a discharge in a gas that is in contact with a liquid, thereby partially ionizing the gas. The gas for forming a plasma by a discharge may be introduced into a space in contact with the surface of a liquid (liquid surface) or may be introduced as bubbles into a liquid. Electrons, ions atoms and molecules in a submerged plasma may interact with a liquid or substances in the liquid through the gas-liquid interface, causing various chemical reactions.

Techniques have been under development for forming a plasma in a liquid in order to improve the water quality or to treat waste liquids. A practical object of such a submerged plasma technique is for example, the decomposition and sterilization of a low-degradable organic substance in an aqueous solution. A low-degradable organic substance, such as dioxin, that cannot be decomposed by ozone can be decomposed by hydroxyl radicals (.OH) formed by a reaction between a plasma and water. This is called an advanced oxidation process, and methods using ultraviolet rays, methods using hydrogen peroxide, etc., are also known in the art.

Discharge for producing a plasma in a liquid is generally classified into direct-current or low-frequency discharge and high-frequency or microwave discharge. Examples of the former include streamer and arc discharge in water using direct-current pulse discharge (see Non-Patent Document No. 1), and dielectric barrier discharge (see Patent Document Nos. 1, 2 and 3). With dielectric barrier discharge, a as is provided between electrodes, and a discharge plasma is induced in the gas. The devices disclosed in Patent Document Nos. 1, 2 and 3 all have a structure in which a 2-phase region of bubbles and water is sandwiched between electrodes. Examples of the latter include RB discharge and microwave discharge. Also in this case, bubbles are employed. Bubbles having been introduced or produced in a liquid, absorb electromagnetic energy, thereby producing a plasma (see Non-Patent Document Nos. 2 and 3). Submerged discharge techniques in general are reviewed in Non-Patent Document No. 2. The disclosures of Non-Patent Document Nos. 1 to 3 are hereby incorporated by reference in their entirety.

CITATION LIST

Patent Literature

[Patent Document No. 1] Japanese Laid-Open Patent Publication No. 2010-133212
[Patent Document No. 2] Japanese Laid-Open Patent Publication No. 2004-268003
[Patent Document No. 3] Japanese Laid-Open Patent Publication No. 2009-114001

Non-Patent Literature

[Non-Patent Document No. 1] "Water Purification by Plasmas: Which Reactors are Most Energy Efficient?" by Muhammad Arif Malik, Plasma Chem Plasma Process (2010) 30:21-31
[Non-Patent Document No. 2] "Generation of Underwater Discharge Plasma and its Property" (Koichi Iasuoka, at al., J. Plasma Fusion Res. Vol. 84, No.10 (2008) 666-673)
[Non-Patent Document No. 3] PLASMA CHEMISTRY by Alexander Fridman, Cambridge University Press, 2008

SUMMARY OF INVENTION

Technical Problem

A primary object of the present invention is to provide a method for more efficiently performing the decomposition and sterilization of a low-degradable organic substance in an aqueous solution by means of a submerged plasma and a submerged plasma device for use with such a method, and to provide a method for synthesizing an organic substance by means of a submerged plasma and a submerged plasma device for use with such a method.

Solution to Problem

The present invention at least provides an organic substance synthesis method, a submerged plasma device, a submerged plasma treatment method and a liquid purification system as defined in the following items.

[Item 1]
An organic substance synthesis method including:
forming a plasma through discharge in a gas including a carbon dioxide gas in contact with water; and
generating an organic substance including performic acid or diformyl peroxide in the water by contact between the plasma and the water.

[Item 2]
The organic substance synthesis method according to item 1, wherein the discharge is dielectric barrier discharge.

[Item 3]
The organic substance synthesis method according to item 1 or 2, wherein the organic substance includes performic acid.

[Item 4]
The organic substance synthesis method according to any one of items 1 to 3, using a submerged plasma device, the submerged plasma device including:
a first electrode;
a solid dielectric layer in contact with the first electrode;
discharge chamber having an inner space accommodating the first electrode and the solid dielectric layer;
a second electrode arranged so as to oppose the first electrode with the solid dielectric layer therebetween and so as to separate the inner space of the discharge chamber from water, the second electrode having a gas phase surface located on a side of the inner space and a liquid phase surface located on a side of the water, and the second electrode having a plurality of through holes connecting together the as phase surface and the liquid phase surface; and
a gas introducing device for supplying a carbon dioxide gas into the inner space of the discharge chamber so as to form an interface between the carbon dioxide gas and the water inside each of the through holes of the second electrode, wherein the organic substance is generated in the water through discharge in the carbon dioxide gas

[Item 5]

A submerged plasma device for causing dielectric barrier discharge, including:

a first electrode;

a solid dielectric layer in contact with the first electrode;

a discharge chamber having an inner space accommodating the first, electrode and the solid dielectric layer;

a second electrode arranged so as to oppose the first electrode with the solid dielectric layer therebetween and so as to separate the inner space of the discharge chamber from a liquid, the second electrode having a gas phase surface located on a side of the inner space and a liquid phase surface located on a side of the liquid, and the second electrode having a plurality of through holes connecting together the gas phase surface and the liquid phase surface; and a gas introducing device for supplying a as into the inner space of the discharge chamber so as to form an interface between the gas and the liquid inside each of the through holes of the second electrode.

[Item 6]

The submerged plasma device according to item 5, wherein the first electrode and the second electrode are each a flat plate.

[Item 7]

The submerged plasma device according to item 5 or 6, wherein an opening size of each of the plurality of through holes is smaller than an interelectrode distance defined by the first electrode and the second electrode.

[Item 8]

The submerged plasma device according to any one of items 5 to 7, wherein an opening size of each of the plurality of through holes is smaller than 0.5 mm.

[Item 9]

The submerged plasma device according to any one of items 5 to 8, including an electrical circuit configured to apply a voltage between the first electrode and the second. electrode so as to cause dielectric barrier discharge,

[Item 10]

The submerged plasma device according to any one of Items 5 to 9, including a tank for at least temporarily accommodating the liquid in a stationary or flowing state, the tank allowing the liquid to be in contact with the liquid phase surface of the second electrode.

[Item 11]

The submerged plasma device according to any one of items 5 to 10, wherein the discharge chamber includes an opening for allowing a part of the gas having been introduced to an inside by the gas introducing device to be discharged into the liquid.

[Item 12]

The submerged plasma device according to any one of items 5 to 11, wherein the liquid is water.

[Item 13]

The submerged plasma device according to item 12, wherein:

the gas introducing device is configured to supply a carbon dioxide gas, as the gas, to an inside of the discharge chamber; and an organic substance including performic acid or diformyl peroxide is generated in the water through discharge in the carbon dioxide gas.

[Item 14]

A submerged plasma treatment method for treating a liquid using the submerged plasma device according to any one of items 5 to 13, the method including:

bringing the liquid into contact with the liquid phase surface of the second electrode;

supplying a gas into the inner space of the discharge chamber by the gas introducing device so as to form an interface between the gas and the liquid inside each of the through holes of the second electrode; and applying a voltage between the first, electrode and the second elect rode so as to cause dielectric barrier discharge, and producing a plasma the gas in the discharge chamber through the dielectric barrier discharge.

[Item 15]

The submerged plasma treatment method according to item 14, wherein bringing the liquid into contact with the liquid phase surface of the second electrode includes arranging the reaction chamber of the submerged plasma device in the liquid.

[Item 16]

A submerged dielectric barrier discharge plasma device capable of causing discharge in a liquid, comprising:

an electrode covered with a dielectric;

an electrode having a plurality of through holes;

an electrode supporting substrate supporting electrode covered with a dielectric; and a pressure control chamber, the electrode covered with a dielectric and the electrode having a plurality of through holes are arranged opposing each other; an opening diameter of the through holes is smaller than an interelectrode distance between the electrode covered with a dielectric and the electrode having a plurality of through holes; a gas introducing port is provided in the electrode supporting substrate; and the pressure control chamber is connected to the gas introducing port.

[Item 17]

The submerged dielectric barrier discharge plasma device according to item 16, wherein the electrode having a plurality of through holes is formed by one or two or more materials selected from the group consisting of an aluminum alloy, a stainless steel, a nickel alloy and a titanium alloy.

[Item 18]

The submerged dielectric barrier discharge plasma device according to item 16, wherein the electrode having a plurality of through holes is a plastic resin or a ceramic material formed with a plurality of through holes and covered with a thin conductive film, which is formed by one or two or more materials selected from the group consisting of an aluminum alloy, a stainless steel, a nickel alloy and a titanium alloy.

[Item 19]

The submerged dielectric barrier discharge plasma device according to item 16, wherein the electrode having a plurality of through holes includes a silicon substrate micromachined to have through holes.

[Item 20]

The submerged dielectric barrier discharge plasma. device according to any one of items 16 to 19, wherein the through holes provided in the electrode having a plurality of through holes have an opening diameter on one side opposing the electrode covered with a dielectric that is greater than an opening diameter on the other side

[Item 21]

The submerged dielectric barrier discharge plasma device according to item 16, wherein the electrode having a plurality of through holes includes a porous material.

[Item 22]

The submerged dielectric barrier discharge plasma device according to any one of items 16 to 21, wherein the electrode covered with a dielectric is formed by a ferritic stainless steel or a martensitic stainless steel and covered with a soda-lime glass.

[Item 23]

The submerged dielectric barrier discharge plasma device according to any one of items 16 to 22, wherein the pressure control chamber has a pressure control mechanism.

[Item 24]

The submerged dielectric barrier discharge plasma device according to any one of items 16 to 23, further comprising a gas introducing pipe for introducing a gas into the pressure control chamber, and a power supply line for supplying power to the electrode covered with a dielectric and the electrode having a plurality of through holes.

[Item 25]

A liquid purification system including: the submerged dielectric barrier discharge plasma device according to any one of items 16 to 24; a gas supply device; and a high-voltage power supply.

Advantageous Effects of Invention

Embodiments of the present invention provide an organic substance synthesis method using a submerged plasma and other treatment methods. Embodiments of the present invention also provide a novel submerged plasma device for use with these methods.

DESCRIPTION OF EMBODIMENTS

A submerged plasma device according to an embodiment of the present invention, a treatment method and an organic substance synthesis method using the submerged plasma device will now be described with reference to the drawings, but embodiments of the present invention are not limited to those illustrated herein.

<Basic Configuration of Submerged Plasma Device>

A submerged plasma device according to an embodiment of the present invention is a plasma device for causing dielectric barrier discharge. As will be described later, the device can suitably be used for synthesizing an organic substance. However, the application of the submerged plasma device is not limited to the synthesis of an organic substance.

Figure 1:
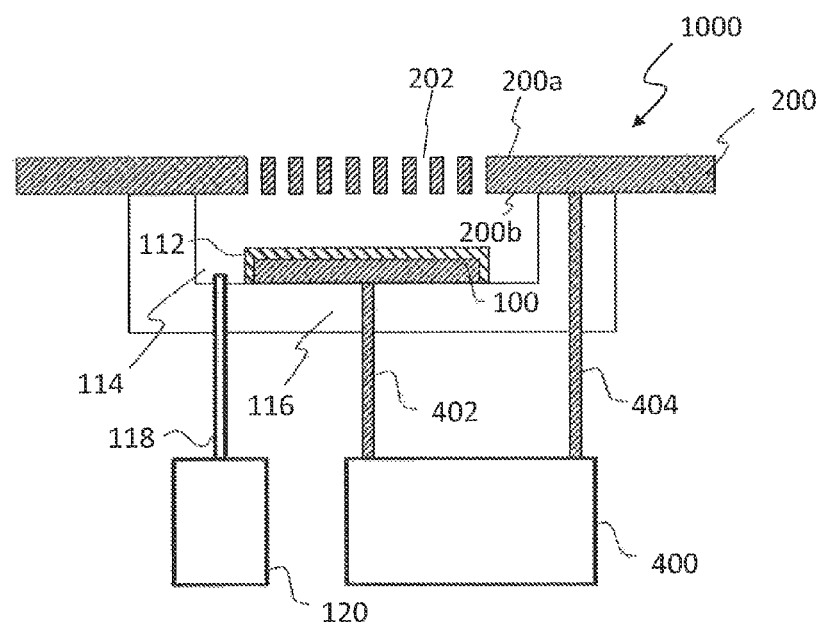
FIG. 1 A cross-sectional view schematically showing a basic configuration of a submerged plasma device 1000 according to an embodiment of the present invention.
Figure 2:
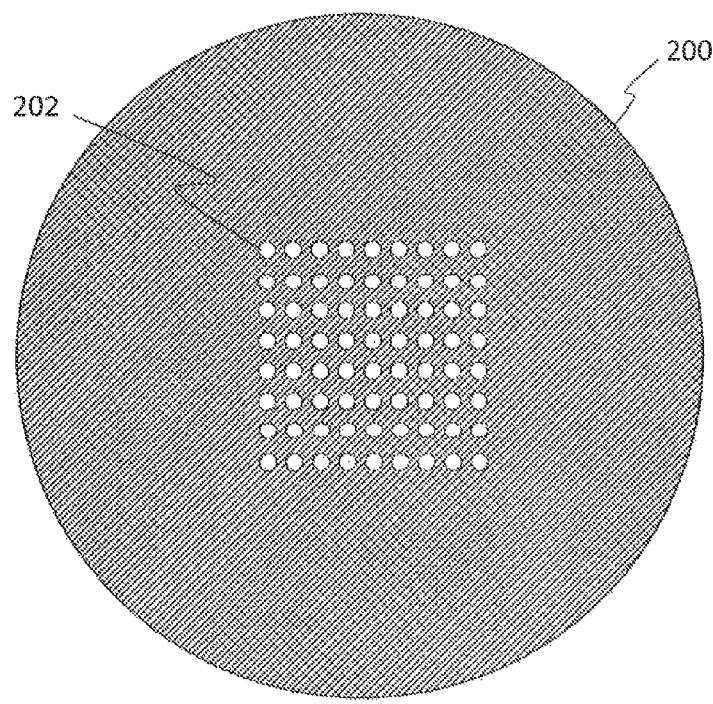
FIG. 2 A top view of the submerged plasma device 1000.

First, referring to FIG. 1 and FIG. 2, a basic configuration of the submerged plasma device 1000 according to one embodiment will be described. FIG. 1 is a cross-sectional view schematically showing the basic configuration of the submerged plasma device 1000. FIG. 2 is a top view of the submerged plasma device 1000.

The submerged plasma device 1000 shown in FIG. 1 includes a discharge chamber 116 having an inner space 114, a first electrode 100 located in the inner space 114 of the discharge chamber 116, and a second electrode 200 opposing the first electrode. A solid dielectric layer 112 in contact with the first electrode 100 is present between the first electrode 100 and the second electrode 200.

Therefore, the second electrode 200 opposes the first electrode 100 with the solid dielectric layer 112 therebetween. A space (gap) for causing discharge is present between the second electrode 200 and the solid dielectric layer 112. The solid dielectric layer 112 may cover the surface of the first electrode 100.

The first electrode 100 and the second electrode 200 are each formed by a conductive material such as a metal. On the other hand, the discharge chamber 116 is formed by an insulating material.

The second electrode 200 is arranged so that the inside of the discharge chamber 116 is separated from a liquid (not shown). The second electrode 200 includes a liquid phase surface 200a located on the outside of the discharge chamber 116, and a gas phase surface 200b located on the inner space 114 side of the discharge chamber 116, and has a plurality of through holes 202 connecting together the liquid phase surface 200a and the gas phase surface 200b. While FIG. 2 shows an example of 72 through holes 202 arranged in an array of 8 rows and 9 columns, the arrangement and the number of through holes 202 are not limited thereto. The arrangement of the through holes 202 may be regular or irregular. The opening size of the through holes 202 may vary depending on the position on the second electrode 200.

Figure 3:
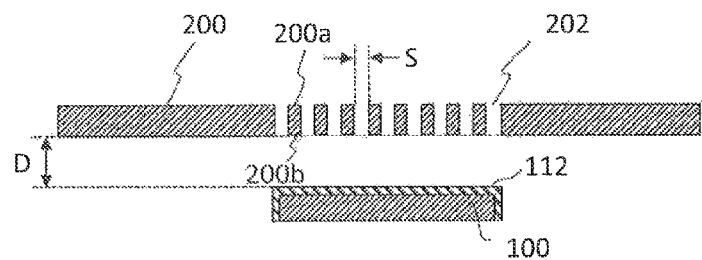
FIG. 3 A cross-sectional view showing the interelectrode distance D.

Reference is made to FIG. 3. FIG. 3 is a cross-sectional view showing the interelectrode distance D. The interelectrode distance D is defined by the first electrode 100 and the second electrode 200. Strictly speaking, the interelectrode distance D is the distance from the gas phase surface 200b of the second electrode 200 to the surface of the solid dielectric layer 112. The size proportion between the first electrode 100, the solid dielectric layer 112 and the second electrode 200 in the figures may not necessarily reflect the actual size proportion. Typically, the thickness of the solid dielectric layer 112 is smaller than the thickness of the first electrode 100. Thus, the interelectrode distance D is substantially equal to the distance between the first electrode 100 and the second electrode 200.

The opening size S of each of the through holes 202 is smaller than the interelectrode distance D. The opening size S of each of the through holes 202 may typically be set to a value smaller than 0.5 mm. The cross section of a through hole 202 on a plane that is perpendicular to the direction in which the through hole 202 extends does not need to be in a circular shape. The shapes of the through holes 202 do not need to be the same or similar.

Reference is made again to FIG. 1. The submerged plasma device 1000 includes a gas introducing device 120 for supplying a gas for causing discharge to the inside of the discharge chamber 116. The gas introducing device 120 of this example can supply a gas into the inner space 114 of the discharge chamber 116 via at least one pipe 118. The gas introducing device 120 may operate so as to form an interface between a gas and a liquid (a gas-liquid interface) inside each through hole 202 of the second electrode 200. The pressure of the gas in the inner space 114 of the discharge chamber 116 can be adjusted appropriately in accordance with the pressure of the liquid on the second electrode 200.

In the example shown in FIG. 1, the first electrode 100 and the second electrode 200 each have a flat plate shape, together forming a parallel plate electrode structure. However, the shape of the first electrode 100 and that of the second electrode 200 are not limited to a flat plate shape. The first electrode 100 and the second electrode 200 do not even need to be parallel to each other. The second electrode 200 shown in FIG. 2 has a generally disc shape, but may have a rectangular shape or any other suitable shape. As the first electrode 100 is seen through the second electrode 200 from the direction vertical to the upper surface of the second electrode 200 (the liquid phase surface 200a), the outline of the second electrode 200 may be the same as, or different from, the outline of the first electrode 100. While the first electrode 100 is shown to be smaller than the second electrode 200 in FIG. 1, the first electrode 100 and the second electrode 200 may have any relationship therebetween.

The first electrode 100 and the second electrode 200 are connected to an electrical circuit 400 via a first electrical conductor 402 and a second electrical conductor 404, respectively as shown in FIG. 1. The electrical circuit 400 may be a high voltage circuit including a booster circuit, for example. The electrical, circuit 400 may be connected to a power source such as a commercial power system, a generator storage battery. The electrical circuit 400 is configured to apply a voltage between the first electrode 100 and the second electrode 200 so as to cause dielectric barrier discharge inside the discharge chamber 116.

Figure 4:
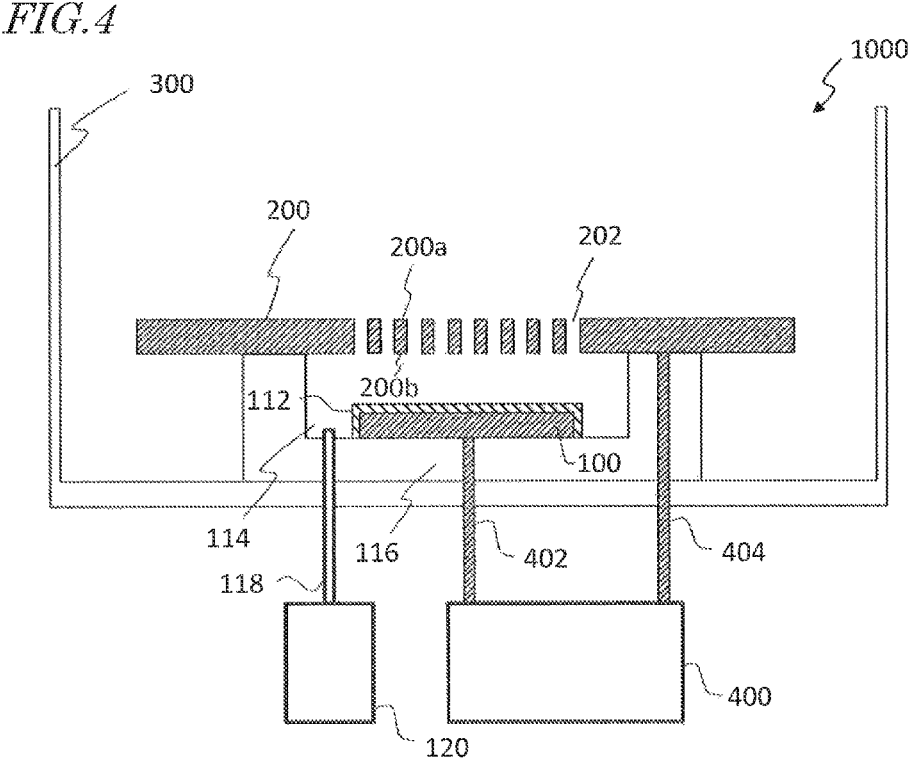
FIG. 4 A cross-sectional view showing an example where the submerged discharge plasma device 1000 includes a liquid tank 300.
Figure 5:
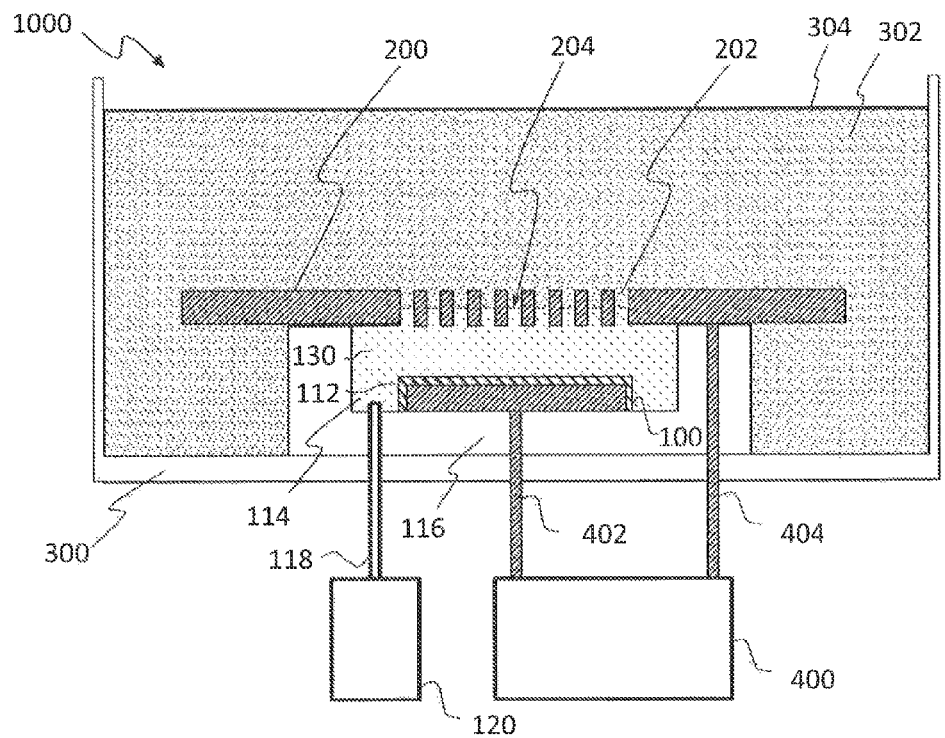
FIG. 5 A cross-sectional view showing a state where a liquid 302 is scored in the liquid tank 300.

Reference is next made to FIG. 4 and FIG. 5. FIG. 4 shows an example where the submerged discharge plasma device 1000 includes a liquid tank 300. FIG. 5 shows a state where the liquid 302 is stored in the liquid tank 300. Thus, the liquid tank 300 is configured to at least temporarily accommodate the liquid 302 in a stationary or flowing state. An upper surface (liquid surface) 304 of the liquid 302 is in contact with the atmospheric air and is under the atmospheric pressure. The gas having been introduced into the inner space 114 of the discharge chamber 116 comes into contact with the liquid 302 inside each through hole 202 of the second electrode 200, thereby forming a contract surface 204. Therefore, the pressure of the gas in he inner space 114 of the discharge chamber 116 has a value that corresponds to the total value of the atmospheric, pressure and the water pressure. Where the gas is intermittently or continuously supplied into the inner space 114 of the discharge chamber 116, a part of the gas is discharged from the inner space 114 of the discharge chamber 116 into the liquid 302. Such a part of the gas may be discharged into the liquid 302 through any of the through holes 202 of the second electrode 200. Thus, the pressure of the gas inside the inner space 114 of the discharge chamber 116 can be kept in balance with the pressure of the liquid 302.

The discharge chamber 116 may have an opening for discharging, into the liquid 302, a part of the gas having been introduced into the inner space 114 by the gas introducing device 120.

Figure 6:
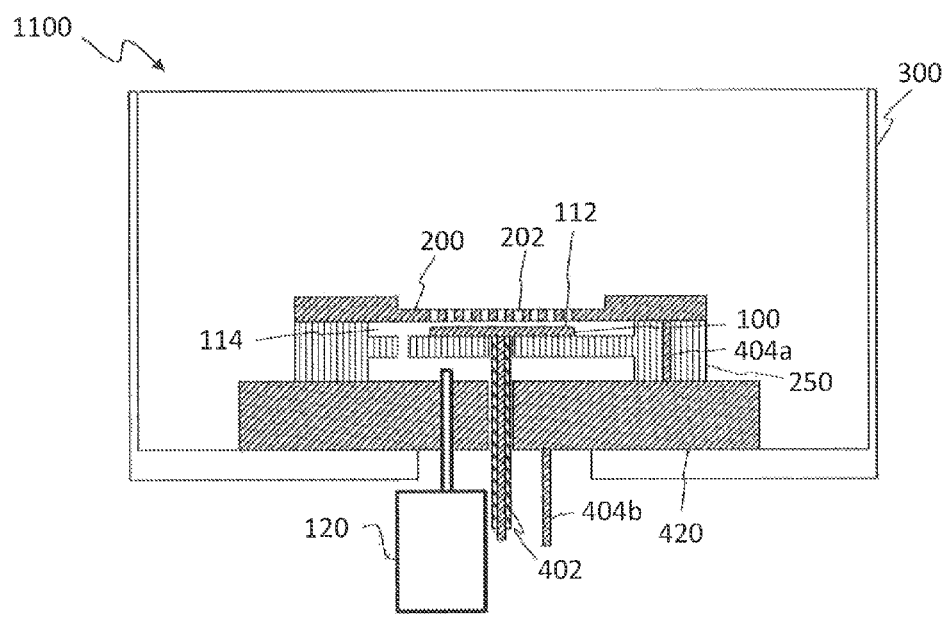
FIG. 6 A cross-sectional view schematically showing primary elements of a submerged plasma device 1100 according to a variation of the embodiment of the present invention.

FIG. 6 is a cross-sectional view schematically showing primary elements of the submerged plasma device 1100 according to a variation of the embodiment of the present invention. The submerged plasma device 1100 has the same basic configuration as that of the submerged plasma device 1000. Like reference numerals denote functionally like elements, which will not be described repeatedly.

The submerged plasma device 1100 shown in FIG. 6 includes an insulating support 250 for supporting the first electrode 100. The insulating support 250 includes a depressed portion forming a space for causing discharge, and a protruding portion defining the interelectrode distance D. The second electrode 200 is supported by the protruding portion.

The insulating support 250 is arranged on a conductive base 420. The conductive base 420 is electrically connected to the second electrode 200 via a conductor 404a provided inside the insulating support 250. The conductive base 420 is connected to a conductor 404b. In such an example configuration, the surface of the conductor 402 is covered with an insulating layer in order to ensure the insulation between the conductor 402 and the conductive base 420. It is possible to cause dielectric barrier discharge by applying a voltage to the conductor 402 and the conductor 404b.

Figure 7:
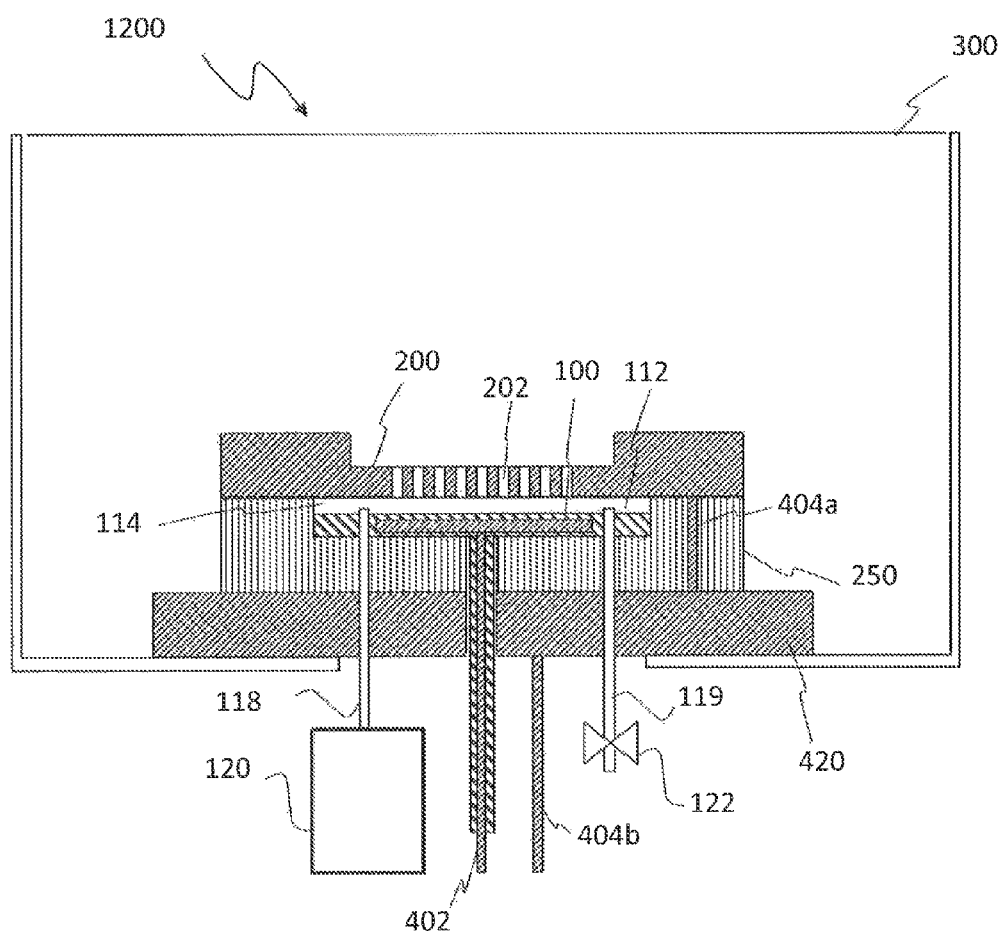
FIG. 7 A cross-sectional view schematically showing primary elements of a submerged plasma device 1200 according to another variation of the embodiment of the present invention.

FIG. 7 is a cross-sectional view schematically showing primary elements of a submerged plasma device 1200 according to another variation of the embodiment of the present invention. The submerged plasma device 1200 is different from the submerged plasma. device 1100 shown in FIG. 6 in that the submerged plasma device 1200 includes the inner space 114 of which at least the bottom surface is substantially flat. The bottom surface of the inner space 114 is formed by the upper surface of the dielectric layer 112 covering the first electrode 100. The dielectric layer 112 or this example includes a portion obtained by expanding the dielectric layer 112 horizontally outward past the circumferential side surface of the first electrode 100. In this portion, the dielectric layer 112 is relatively thick. The pipe 118 for supplying the gas for causing discharge into the inner space 114 runs through a portion of the dielectric layer 112 where the first electrode 100 is absent.

The submerged plasma device 1200 includes a discharge pipe 119 and a valve 122 through which a liquid and/or gas, having entered the inner space 114, can be discharged to the outside of the inner space 114. The liquid 302 having been supplied into the liquid tank 300 may possibly enter the discharge space 114 before starting discharge or while discharge is being interrupted. When the gas is supplied into the inner space 114 via the pipe 118, it is possible to discharge the liquid 302 of the inner space 114 via the discharge pipe 119 by opening the valve 122. By using such a discharge pipe 119, it is possible to fill the inside of the inner space 114 with the gas, making easer to cane discharge. In addition, any reaction product formed inside the discharge space 114 can be taken out to the outside in gas phase.

As described above, the internal pressure of the inner space 114 can be adjusted by the flow rate of the gas supplied from the gas introducing device 120 into the inner space 114. As described above, the pressure of the gas in the inner space 114 has a value that corresponds to the total value of the atmospheric pressure and the water pressure. Therefore, it is possible to increase the upper limit value of the pressure of the gas in the inner space 114 by adding pressurization on the liquid 302.

Figure 8:
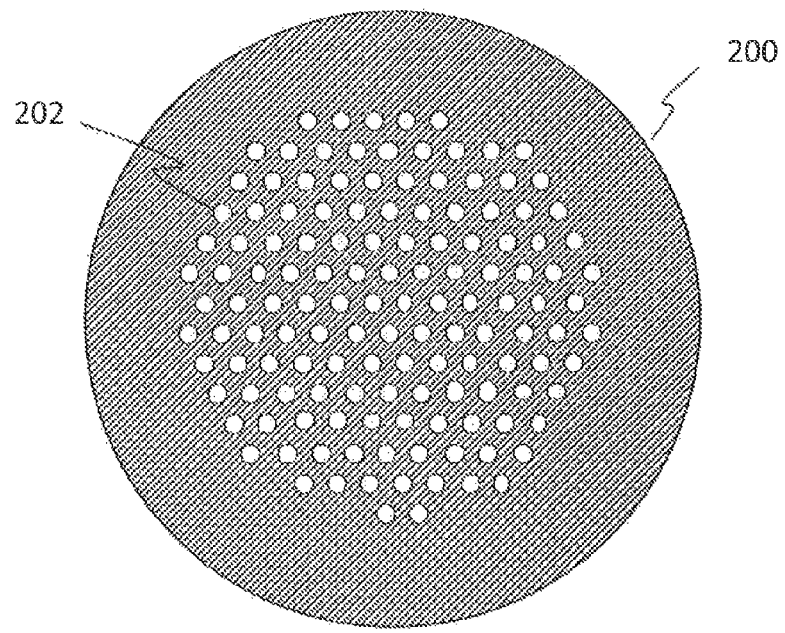
FIG. 8 (*a*) is a top view showing an example arrangement of through holes 202 in a second electrode 200, and (*b*) is a cross-sectional view showing an example where a solid dielectric layer 212 is provided covering the second electrode 200.
Figure 8:
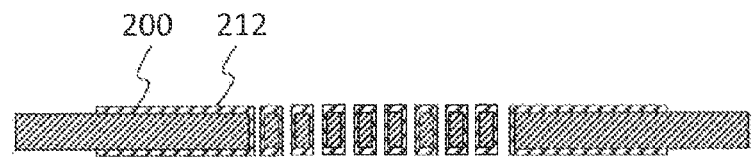

FIG. 8(a) is a top view showing another example arrangement of the through holes 202 in the second electrode 200. The area of the contract surface 204 between the gas and the liquid 302 is in proportion to the aperture ratio of the through holes 202 in the second electrode 200 (see FIG. 29). With the through holes 202 arranged in a honeycomb pattern, it is possible to easily increase the aperture ratio while maintaining the mechanical strength of the second electrode 200.

FIG. 8(b) is a cross-sectional view showing an example where the solid dielectric layer 212 is provided covering the second electrode 200. As shown in FIG. 8(b), the solid dielectric layer 212 may be provided so as to cover a portion that contributes to the discharge of the second electrode 200. The solid dielectric layer 212 is formed to partially expose the second electrode 200 so as to realize contact between the second electrode 200 and water.

<Submerged Plasma Device>

An embodiment of a submerged plasma device will now be described in detail.

Figure 9:
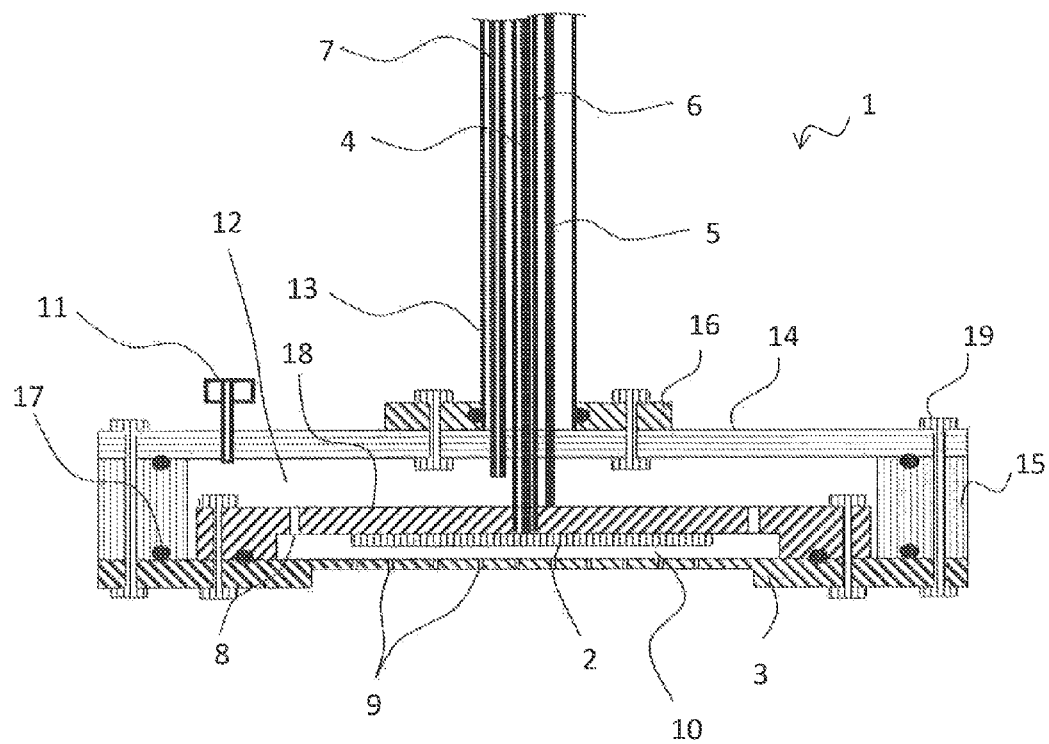
FIG. 9 A diagram showing a submerged dielectric barrier discharge plasma device.

FIG. 9 shows a cross-sectional structure of a submerged plasma device 1 according to the embodiment of the present invention. A discharge section 10 is a space sandwiched between an electrode 2 covered with a dielectric and an electrode 3 having a plurality of through holes, and the gap length thereof is 1 mm or less. The "gap length" is the distance from the surface of the dielectric on the electrode 2 to the surface of electrode 3. This distance is equal to the interelectrode distance D described above. The gab length may be set to 0.5 mm±0.1 mm, for example.

The airtightness of the space surrounded by an electrode supporting substrate 18 and the electrode 3 having a plurality of through holes is kept by an O-ring 17. A gas to be the material of a plasma is guided by a gas introducing pipe 7 into a pressure control chamber 12, and is introduced into the discharge section 10 through a gas introducing port 8 provided in the electrode supporting substrate 18. The as becomes a plasma gas in the discharge section 10, and is then discharged into a liquid through through holes 9 provided in the electrode 3 having through holes. Then, the plasma comes into contact with a liquid in the through holes 9. Stopping the intrusion of a liquid into the discharge section 10 can be achieved by adjusting the gas pressure by means of a pressure control mechanism 11. This adjustment can be made easier by providing the pressure control chamber 12.

It is important to keep the liquid surface within the through hole 9 and to prevent the intrusion of a liquid into the discharge section 10. Where a liquid intrudes into the discharge section 10 and wets the electrode surface, if the liquid is conductive, no electric field is produced in a bubble 20 due to electrostatic shielding.

Figure 10:
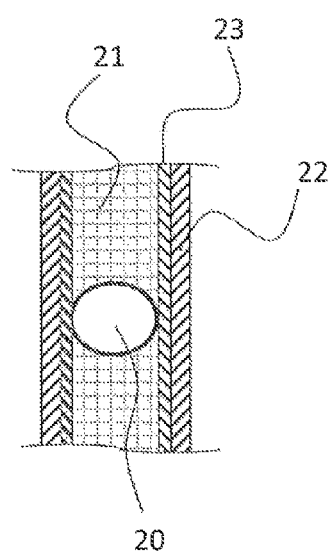
FIG. 10 A diagram showing a part of an electrode portion of the submerged dielectric barrier discharge plasma device.

Even if the bubble 20 is produced in apart, the space between electrodes to cause discharge as shown in FIG. 10, other opposing electrode surfaces are shorted together by the conductive liquid, thereby increasing the load capacity and increasing the power supply capacity. Pressure adjustment is needed to prevent the intrusion of a liquid in the submerged plasma device of the present embodiment.

In order to prevent a liquid from intruding into the discharge section 10, it is effective to appropriately determine the opening diameter of the through hole 9. Through many experiments and researches, we found that it is reasonable that the opening diameter of the through hole 9 is less than or equal to the interelectrode distance.

Figure 11:
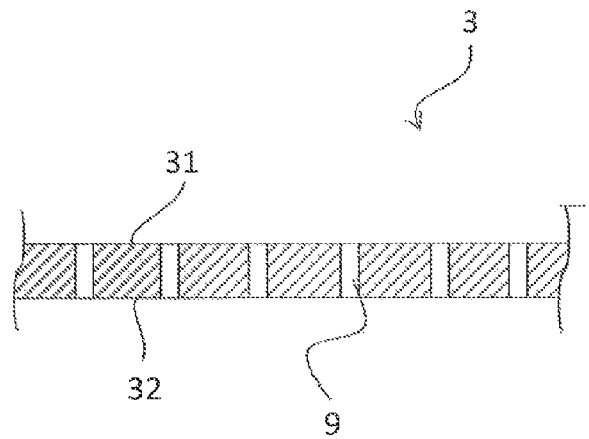
FIG. 11 A diagram showing the structure of an electrode having a plurality of through holes.

FIG. 11 shows a cross-sectional view of the electrode 3 having a plurality of through holes according to the present embodiment. The electrode 3 may be used while being grounded. Since the electrode 3 with a plurality of through holes has openings, the electrode 3 is preferably formed by a metal material having an electrical conductivity, a good thermal conductivity, a good corrosion resistance and is good workability. Specifically, it may be an aluminum alloy, a stainless steel, a nickel alloy, a titanium alloy, etc. Composite materials may also be used. Specifically an example is a plastic resin or ceramic plate formed with many holes therein and coated with a thin conductive film.

Figure 12:
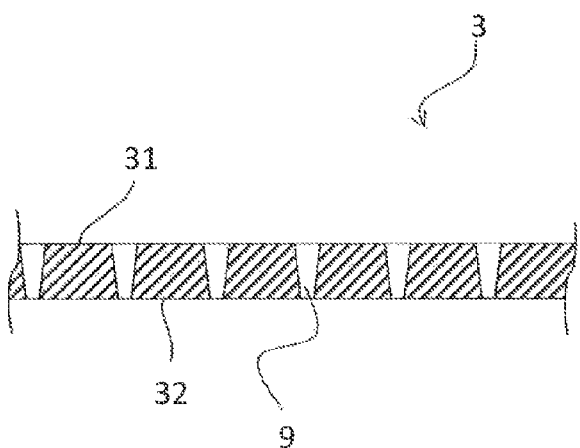
FIG. 12 A diagram showing the structure of an electrode having a plurality of through holes.

With the device 1 of the present embodiment, if the opening diameter of the through holes in the electrode is made too small, one concern is that the liquid intrusion may occur due to surface tension. In order to prevent this, it is effective that the through holes 9 are formed with a sloped side surface so that the diameter thereof gradually increases from a liquid phase surface 32 toward a gas phase surface 31, as shown in FIG. 12. This is effective also for reducing the pressure loss.

Figure 13:
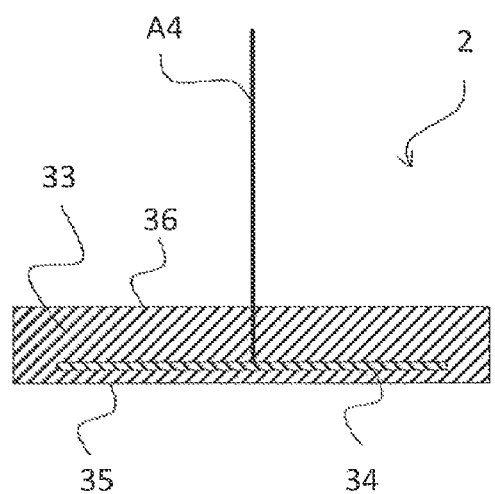
FIG. 13 A diagram showing a structure of an electrode covered with a dielectric.

FIG. 13 shows a cross-sectional structure of the electrode 2 covered with a dielectric according to the present embodiment. A high voltage may be applied to the electrode 2. The electrode 2 includes a metal portion 34 and a dielectric portion 33, and is connected to a power supply line 4.

A portion (solid dielectric layer) of the dielectric portion 33 that is located on the side of discharge surface 35 is preferably as thin as possible so that the voltage applied to the discharge section 10 is higher. The thickness of the solid dielectric, layer is determined by taking into consideration the dielectric strength voltage, the thickness controllability, the mechanical strength and the workability of the dielectric portion 33. A portion of the dielectric portion 33 that is located on the side of a support surface 36 is preferably thick in order to reduce the load capacity and to avoid the application of a high voltage to the electrode supporting substrate 18.

The material of the metal portion 34 preferably has a small thermal expansion coefficient difference relative to the material of the dielectric portion 33. It is beneficial in practice that it has a good adhesion with the dielectric portion 33; it is easily workable; and it can be worked to be connected to the power supply line 4. Through experiments and researches, we found that an epoxy resin, a borosilicate glass or a soda-lime class may be used suitably as the material of the dielectric portion 33 The material of the metal portion 34 may be a 42 alloy an iron alloy containing 42% by mass of nickel), a ferritic stainless steel (SUS403 type), or a martensitic stainless steel (SUS410 type) plate. It can be formed by thermocompression-bonding the dielectric portion 33 on the metal portion 34. In a specific example of the embodiment of the present invention, the dielectric thickness on the discharge surface 35 side was 0.1 mm, and the dielectric thickness on the support surface 36 side was 2 mm. The thickness of the metal portion 34 (stainless steel plate) was 0.1 mm. In addition, a ceramic may be used as a dielectric, and a semiconductor may be used as a conducting substance replacing a metal. These materials may be formed by using a film formation method such as plating, CVD, vapor deposition, thermal, oxidation, printing, etc.

The electrode supporting substrate 18 and a side wall 15 preferably exhibit a good electrical insulation even when a high voltage is applied between the electrode 2 and the electrode 3. The electrode supporting substrate 18 and the side wall 15 may be formed by a resin with a good workability. A ceramic may also be used. Particularly, the electrode supporting substrate 18 is required to be resistant against plasma. Taking into consideration a temperature increase, due to discharge, in the electrode 2 covered with a dielectric, the electrode supporting substrate 18 may be formed by a material having a good heat-resisting property.

Where the submerged plasma device of the present embodiment, is used for a water treatment application, the electrode supporting substrate 18 preferably does not deform at a temperature of 100° C. Specifically, the electrode supporting substrate 18 can be formed by a fluorine-based resin, a polyacetal-based resin, a polyphenylene sulfide resin, or the like.

In the present embodiment, an upper plate 14 is connected to the electrode 3 via the side wall 15. More specifically, the upper plate 14 and the electrode 3 are attached together by metal bolts and nuts 19 running through through holes in the side wall 15. In such a case, the upper plate 14 may be formed by an insulating material such as a resin or a ceramic. Where the upper plate 14 is fixed to the side wall 15 by an insulative method of attachment, instead of using the metal bolts and nuts 19, the upper plate 14 may be formed by a metal material such as an aluminum alloy or to stainless steel.

Figure 14:
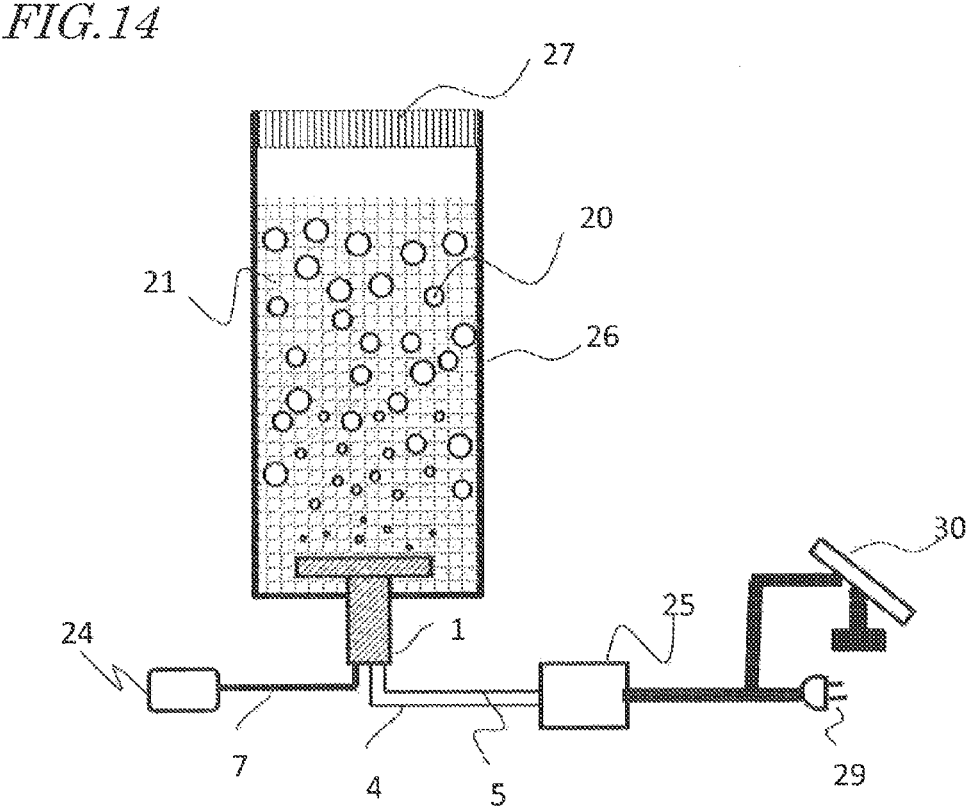
FIG. 14 A diagram showing the device being used in a liquid.

FIG. 14 is a diagram showing an embodiment of a submerged plasma treatment system having a submerged plasma device, according to the present invention.

A liquid treatment tank 26, to which the submerged plasma device 1 is attached, is filled with a liquid 21 to be treated. A as is sent from a gas supply device 24 into the device 1 through the gas introducing pipe 7. A plasma is generated in the device 1, and the plasma comes into contact with the liquid 21 and plasma reaction products such as active species generated are sent out into the liquid 21 in the form of bubbles 20. The bubbles 20 rise and diffuse through the liquid 21 to be discharged to the outside, passing through a filter 27. The filter 27 is provided in order to capture hazardous substances in the discharged gas.

The power for causing discharge is supplied from a high-voltage power supply 25 to the device 1 through the power supply line 4 and a power supply line 5. The power supply may be a commercial power supply 29 or may be a solar cell 30. Where this treatment system is installed outdoors and its constant operation is desired, it is reasonable to employ a power supply using the solar cell 30 baring an auxiliary power supply. For treating a liquid using ozone, the gas supply device 24 may be an air pump or an oxygen supply device. The filter 27 may be an ozone decomposition filter.

Figure 15:
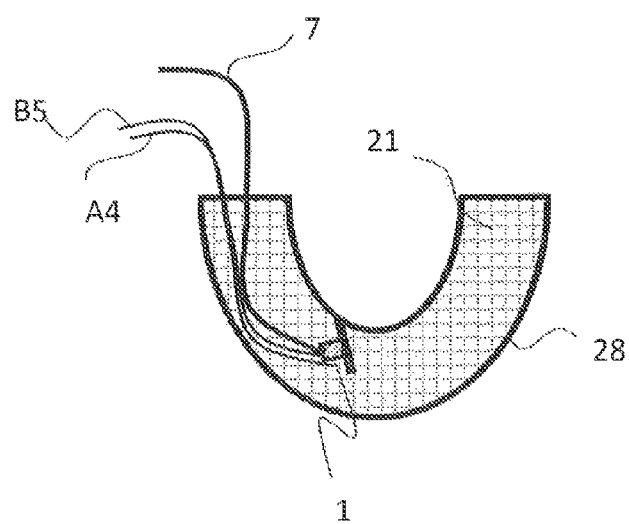
FIG. 15 A diagram showing the device being used in a pipe.

FIG. 15 shows an embodiment where the submerged plasma device 1 is used in a local space. The submerged plasma device 1 is inserted in a pipe 28. In this embodiment, power and a gas to be the plasma material are supplied from the power supply line 4, the power supply line 5 and the gas introducing pipe 7, and the liquid 21 is subjected to a plasma treatment. As shown in the figure, submerged plasma device 1 can be installed at a specific point such as an area where a liquid is held.

<Example of Water Treatment>

Figure 16:
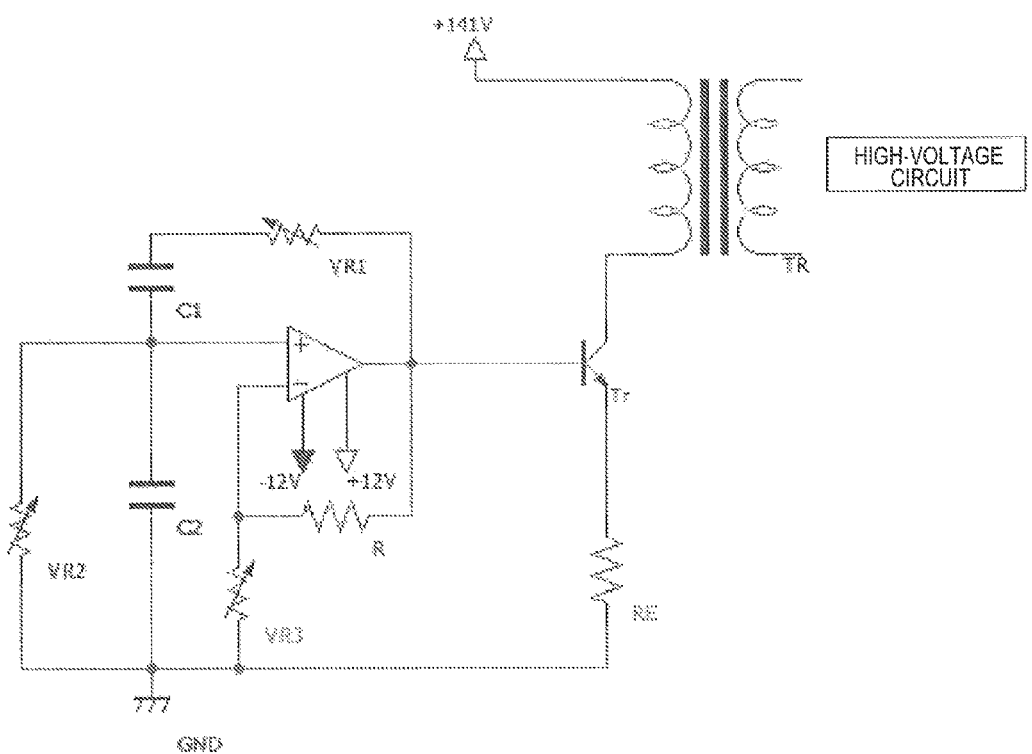
FIG. 16 A diagram showing a high voltage generation circuit.

A dye methylene blue was decolorized using the device 1 of FIG. 9. FIG. 16 shows a configuration of a high. voltage driving circuit used in this example. The oscillation circuit is a Wien bridge circuit for adjusting the oscillating frequency and the gain with a variable resistor. The oscillating frequency used in this example was 26 kHz. The size of the metal portion of the electrode 2 covered with a dielectric was 2 cm×2 cm, the thickness of the dielectric on the discharge surface side was 1 mm, the thickness of the dielectric on the support substrate side was 2 mm, and the dielectric electrode capacitance was 20 pF. A ferritic stainless steel was used as the metal portion and a soda lime glass plate as the dielectric portion, and they were molded, together by thermocompression bonding.

The interelectrode distance was 0.5 mm. The electrode supporting substrate 18, The upper plate 14 and the side wall 15 were produced by using a polyacetal resin plate. The power supply was obtained by rectifying a commercial 100 V AC, and the winding ratio of the high-voltage transformer was set to 1:28. The discharge voltage was 2.8 kV, and the apparent power was 10 W. An air pump with a discharge rate of 3500 cc/min was used as the gas supply device 24.

Figure 17:
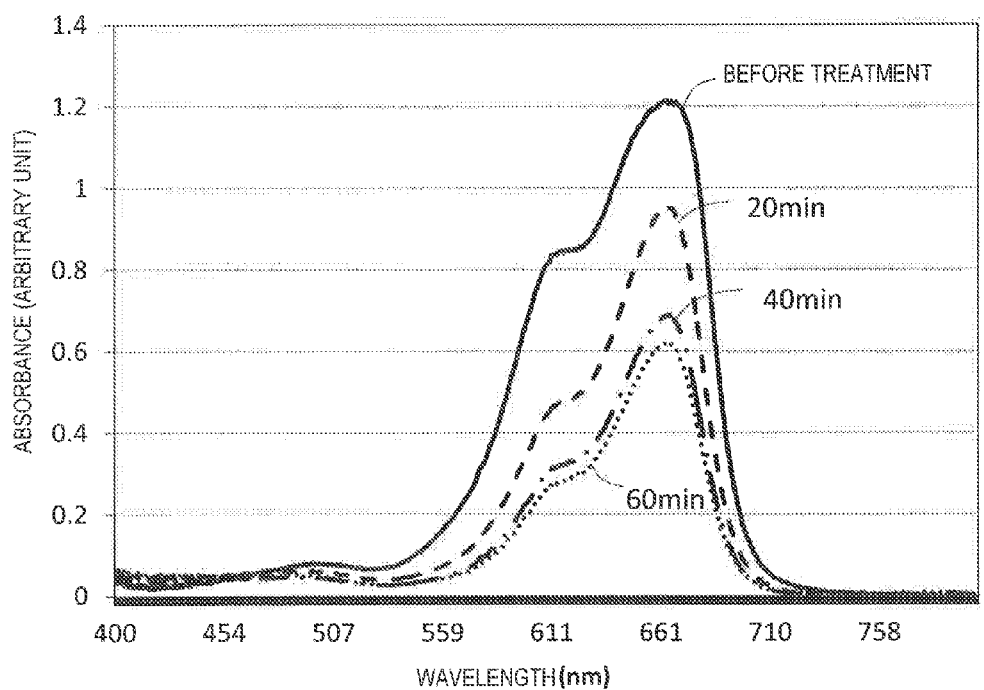
FIG. 17 A graph showing results of methylene blue dye decomposition.
Figure 18:
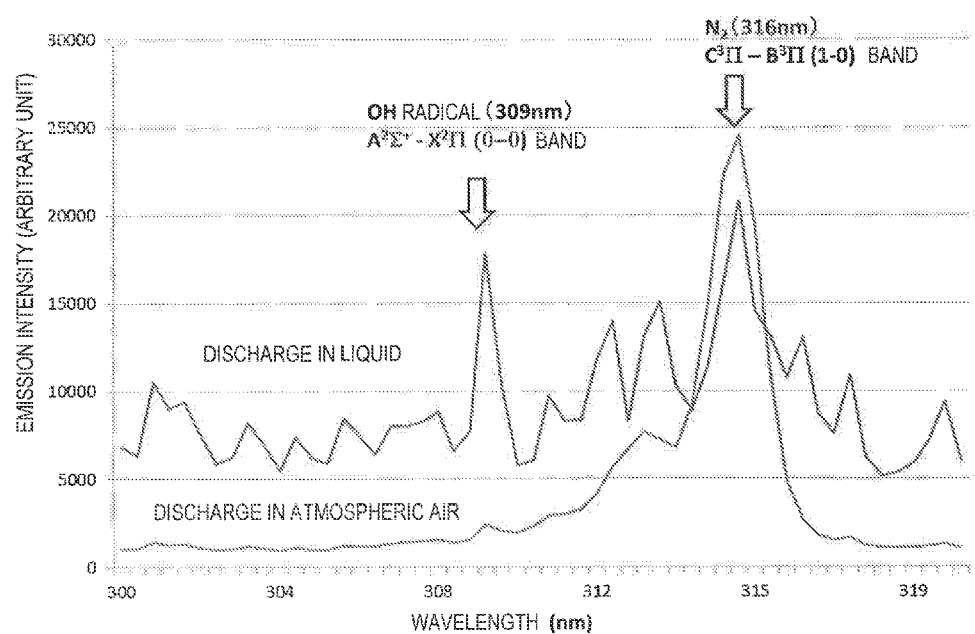
FIG. 18 A graph showing results of an emission spectroscopy of a submerged plasma.

These were used in an overall configuration as shown in FIG. 14, and a dye methylene blue was decolorized. FIG. 17 shows the change over time of the spectral transmission characteristics of the treated liquid. The methylene blue decomposition. energy efficiency calculated from these results was 0.180 g/kWh. This chemical reaction occurred due to an interaction of oxidizing active species generated by the discharge plasma. The obtained efficiency is higher than. the previously reported results using pulsed corona discharge by a factor of about two to three (see Non-Patent Document No. 3). FIG. 18 shows the results of an emission spectroscopy of a submerged plasma, measured in this example, in comparison with those of an atmospheric plasma. An evident generation of hydroxyl radicals is observed for the submerged discharge.

Using the submerged plasma device of this example in an ozone treatment realizes an improvement in the energy efficiency, as compared with conventional ozone treatment devices. This will now be described.

The amount of ozone derived from Chemical Reaction. Formula (I) below is 1.25 g/kWh.

$$3/2 O_2 \rightarrow O_3 \; \Delta H = 1.5 \text{ eV} \qquad (I)$$

The amount of ozone generated by dielectric barrier discharge using oxygen as the material was about 0.05 g/kWh to about 0.07 g/kWh in the prior art. The energy efficiency was 4% to 6%, The efficiency is 2% to 3% when the air is used as the material. This is because nitrogen in the air contributes to the three-body reaction.

The biggest reason for the energy efficiency of conventional ozone treatment devices to be low is in the reaction mechanism. Referring to theories and experimental results, one can expect up to 30% of the theoretical efficiency (see Non-Patent Document No. 3). However, the efficiency of actual ozone treatment devices in use is lower than the theoretical efficiency. This is because ozone disappears through decomposition while being transported from the generation field to the reaction The main reason for this is the decomposition of ozone molecules upon collision with the transport pipe wall or other particles, and the facilitation of the decomposition clue to an increase in the temperature. Moreover, in a practical system, there is a great incidental power load from the gas circulation pump, the cooler, etc., thereby further lowering the energy efficiency of the system. As the energy efficiency is lowered, the device becomes large-scale, and applications thereof will, therefore be limited to large-scale plants.

Using the submerged plasma device according to the present embodiment, it is possible to reduce the power supply capacity and widen the plasma reaction area. The breakdown field strength of water is 1 MV/cm or more Producing streamer discharge in water by direct-current pulse discharge requires a voltage supply of 20 kV or more even when one makes use of the electric field concentration effect. In order to widen the discharge reaction area, it is necessary to enlarge the electrode area. This increases the cower supply capacity, and the device becomes large-scale.

Introducing bubbles into water facilitates discharge. With dielectric barrier discharge, the starting voltage can be reduced, but it is preferred to keep the interelectrode distance short. Dielectric barrier discharge is considered streamer corona discharge. The discharge starting voltage required is lower than the value (Vs) given by Expression (1) below of the Paschen's equation.

$$Vs = Bpd/\ln(Apd/\ln(1+1/\gamma)) \qquad (1)$$

A, B: constants
p: pressure
γ: γ coefficient
d: discharge gap length

With conventional submerged dielectric barrier discharge, however, a 2-phase mixed region of bubbles and a liquid exists between the electrodes. As a result, the load capacity increases. Moreover, it is necessary to form a 2-phase flow by using an external power. On the other hand, when causing high-frequency discharge, Vs decreases due to trapping of electric charges in the bubbles. However, the absorption of the high-frequency power by the plasma increases, thereby increasing the power supply capacity.

According to the embodiment of the submerged plasma device of the present invention, at least one of the following advantageous effects will be realized.

1) In submerged dielectric barrier discharge, discharge plasma is generated stably and steadily.

2) Plasma is allowed to stably come into contact with liquid.

3) It is possible to reduce size and weight, and to lower power consumption.

<Variation>

Figure 19:
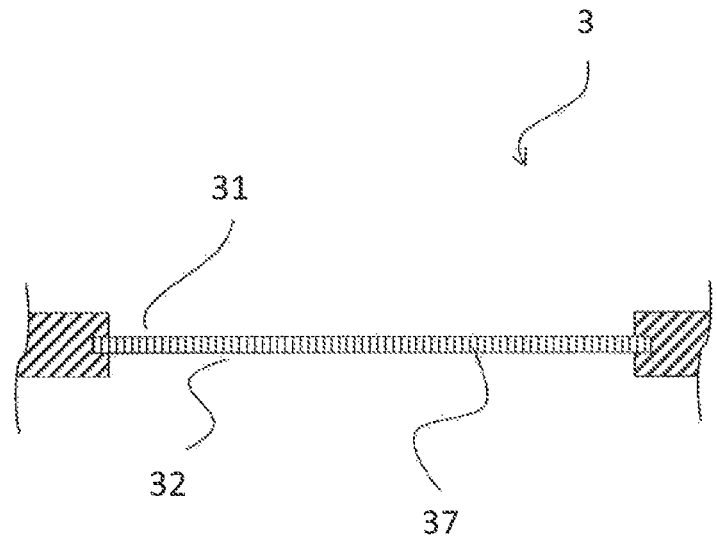
FIG. 19 A diagram showing a structure of an electrode having a plurality of through holes using a porous material.
Figure 20:
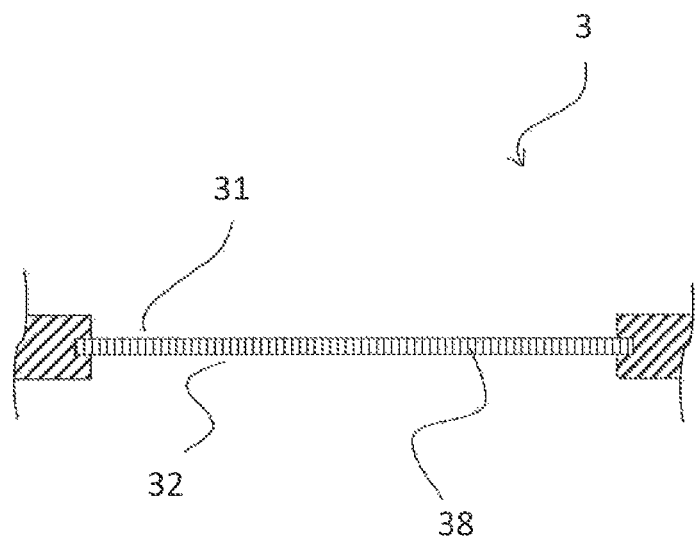
FIG. 20 A diagram showing a structure of an electrode having a plurality of through holes using a silicon substrate that is micromachined to have through holes.

FIG. 19 and FIG. 20 each show a structure of the electrode 3 having a plurality of through holes, of which one component is a porous material, or a silicon substrate that is micromachined to have through holes. With either structure, a good discharging property was obtained. With a porous material, good discharge was realized whether it was a bulky, powdery or fibrous material. In this case, if the material is electrically non-conductive, the liquid to be treated, which is electrolytic, provides electrical conductivity, thereby making it an electrode.

In one embodiment, the submerged plasma device of the present invention is a submerged dielectric barrier discharge plasma device including an electrode covered with a dielectric, an electrode having a plurality of through holes, an electrode supporting substrate supporting the electrode covered with a dielectric, and a pressure control chamber. In this embodiment, the electrode covered with a dielectric and the electrode having a plurality of through holes are arranged opposing each other. A gas introducing port is provided in the electrode supporting substrate. The pressure control chamber is connected to the gas introducing port. The pressure control chamber may have a pressure control mechanism. It may include a gas introducing pipe for introducing a gas into the pressure control chamber, and a power supply line for supplying power to either electrode.

A liquid purification system according to an embodiment of the present invention includes the submerged dielectric barrier discharge plasma device set forth above, a as supply device and a high-voltage power supply.

[Synthesizing Organic Substance]

We made an attempt to synthesize an organic substance from carbon dioxide and water by using the submerged. discharge plasma device 1000 shown in FIG. 4. There has been no report yet reporting the synthesis of an organic substance using a submerged discharge plasma.

Using the submerged discharge plasma device 1000, with water as the liquid 302 stored in the liquid tank 300, as shown in FIG. 5, a power of 20 W (AC 100 V, 0.2 A) was input while supplying a carbon dioxide gas at 1 L (liter)/min from the gas introducing device 120, thereby producing a discharge plasma in water. As a result, it was confirmed that at least one organic substance selected from the group consisting of performic acid, diformyl peroxide and formic acid had been generated in water.

A high-performance liquid chromatograph (LC-10 from Shimadzu Corporation) was used to identify the organic substance generated in water. Develosil RPAQEOUS-AR-5 (from Nomura Chemical) was used for the column, and a 50 mM phosphate buffer (pH 2.4) for the mobile phase, and the oven temperature was set to 40° C. As a. standard sample of formic acid, an aqueous solution obtained by diluting, 1000 times, a. guaranteed reagent (88%) from Wako Pure Chemical Industries was used. Since performic acid is not commercially available, a performic acid aqueous solution prepared by the method described in R. Gehr, P. Chen, and N. Noreen, Water Science and Technology, 59(1), 89-96, 2009) was used as a standard sample, The aqueous solution including performic acid is a mixed aqueous solution of formic acid, hydrogen peroxide, sulfuric acid and performic acid, and the initial concentrations (those when performic acid is not generated) of the components included the mixed aqueous solution are formic acid (9.9M), hydrogen peroxide (4.7M) and sulfuric acid (0.77M), and it is therefore estimated that about 20% of the formic acid is converted to performic acid.

Figure 21:
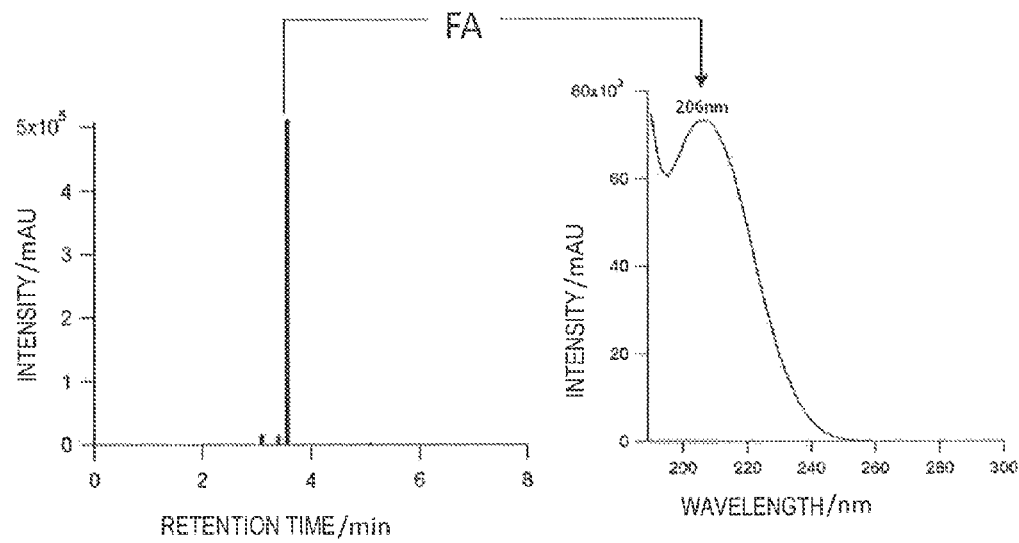
FIG. 21 Graphs showing results of analyzing a standard sample of formic acid by means of a high-performance liquid chromatograph, showing the retention time and the UV spectrum.
Figure 22:
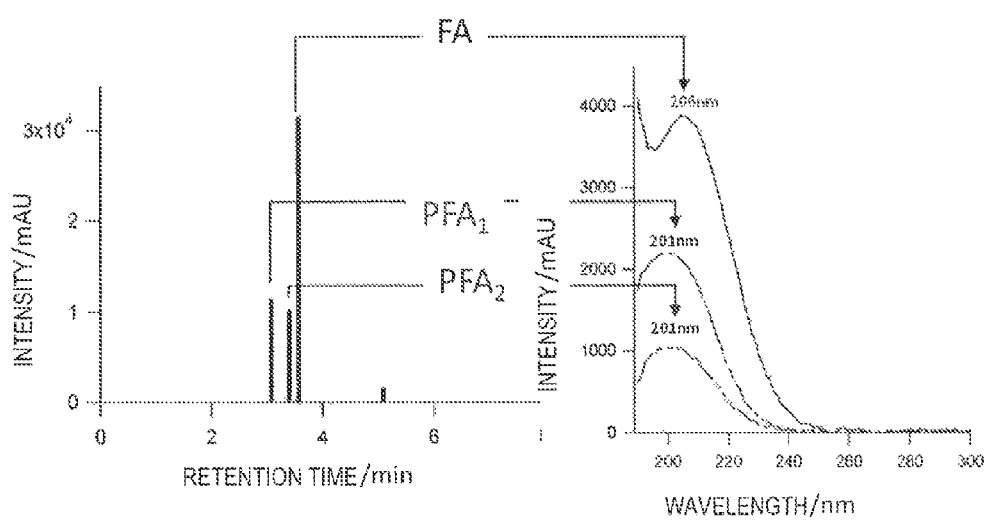
FIG. 22 Graphs showing results or analyzing a standard sample including performic acid by means of a high-performance liquid chromatograph, showing the retention time and the UV spectrum.

The measurement results (the retention time and the UV spectrum) for the standard samples described above are shown in FIG. 21 and FIG. 22, Based on the results for these standard samples, we identified organic substances generated by a submerged discharge plasma.

Figure 23:
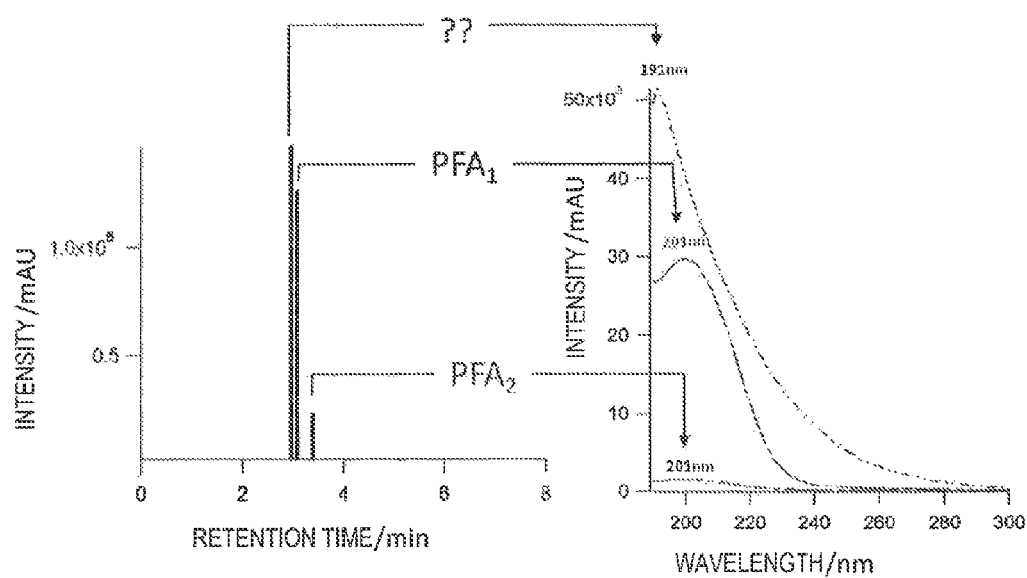
FIG. 23 Graphs showing results of analyzing a sample of which the discharge time is 5 minutes by means of a high-performance liquid chromatograph, showing the retention time and the UV spectrum.
Figure 24:
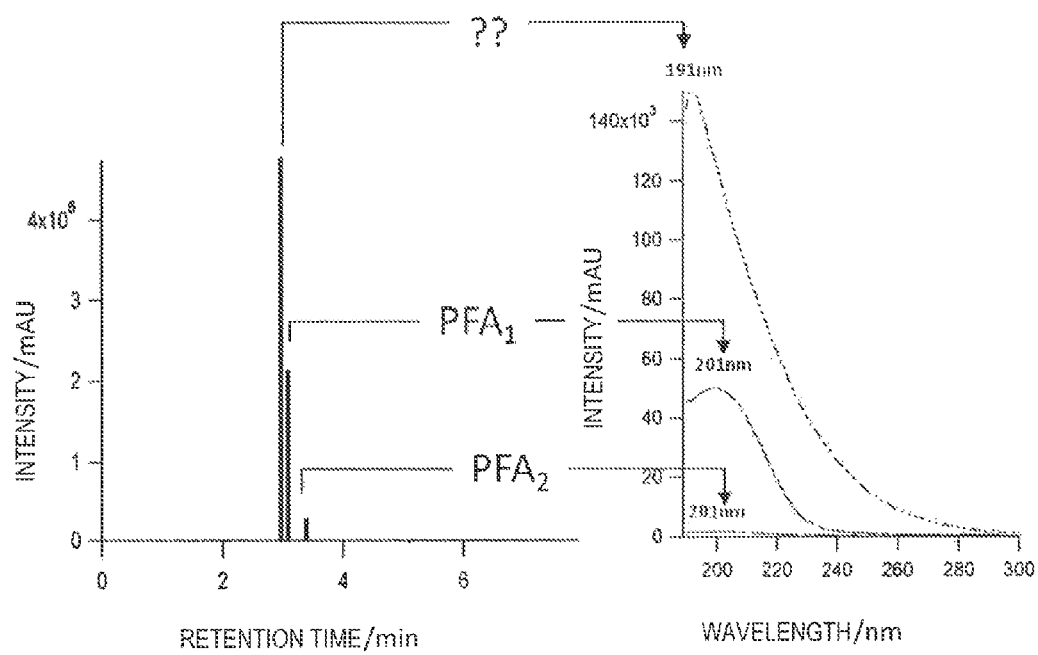
FIG. 24 Graphs showing results of analyzing a sample of which the discharge time is 20 minutes by means of a high-performance liquid chromatograph, showing the retention time and the UV spectrum.

The measurement results for a sample of which the discharge time is 5 minutes and sample of which the discharge time is 20 minutes are shown in FIG. 23 and FIG. 24.

As is clear from FIG. 23 and FIG. 24, performic acid (PFA) was generated by a submerged discharge plasma, and the amount of performic acid generated increased as the discharge time increased. An organic substance of which the retention time is shorter than performic acid and has a strong UV absorption at 191 nm was generated, and the amount of this organic substance generated also increased. as the discharge time increased.

In order to identify an organic substance having an absorption at 191 nm, the mass was determined by matrix-assisted laser desorption ionization/time-of-flight mass spectrometry, MALDI TOF-MS from Shimadzu Corporation was used in the mass spectrometry, and the measurement was performed both in the negative mode and in the positive mode. DHBA (2,5-Dihydroxybenzoic acid) was used as the matrix substance. Samples used were the aqueous solution including per formic acid and the sample of which the discharge time is 20 minutes, which are mentioned above as standard samples. The measurement results are shown in FIG. 25 and FIG. 26.

Figure 25:
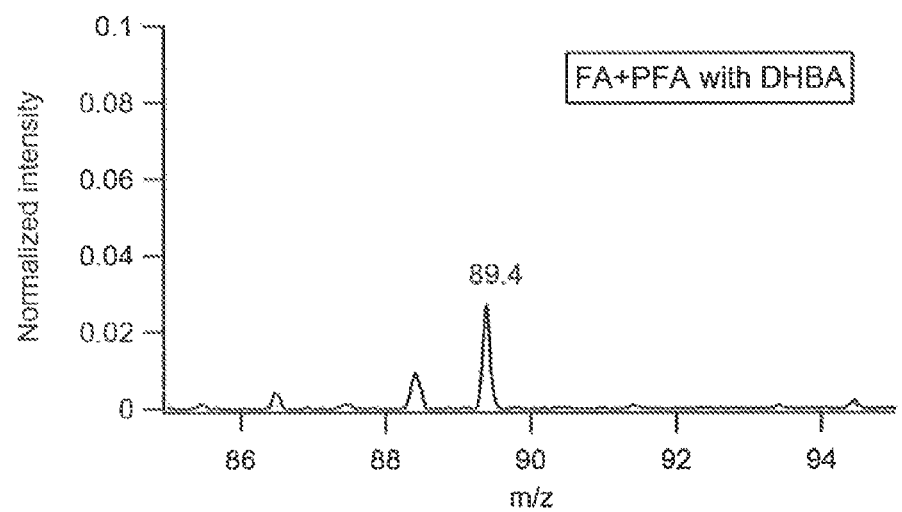
FIG. 25 Graphs showing mass spectrometry results for standard aqueous solution including performic acid by means of matrix-assisted laser desorption ionization time-of-flight mass spectrometry, wherein (a) shows measurement results in the positive mode and (b) shows measurement results in the negative mode.
Figure 25:
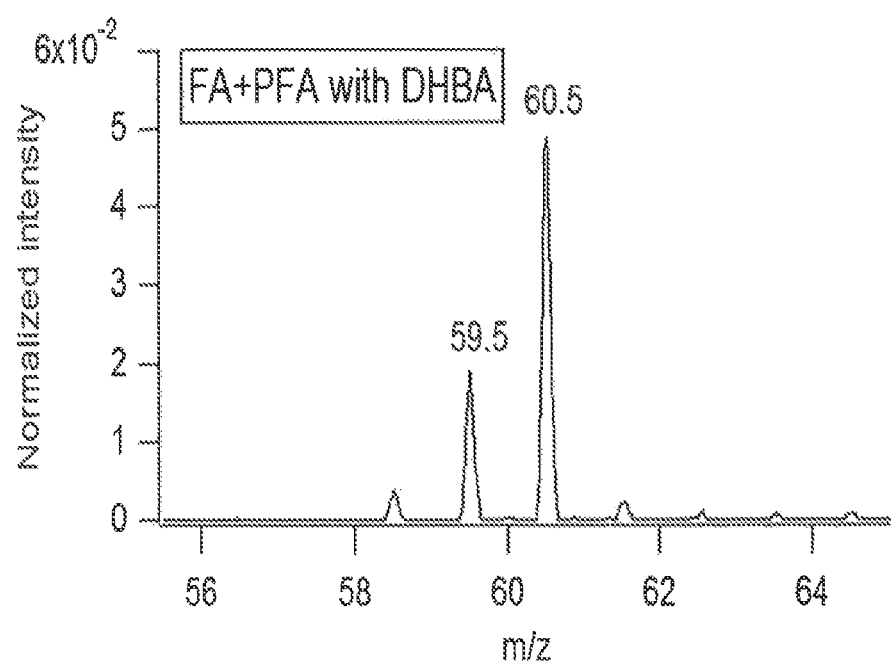
Figure 26:
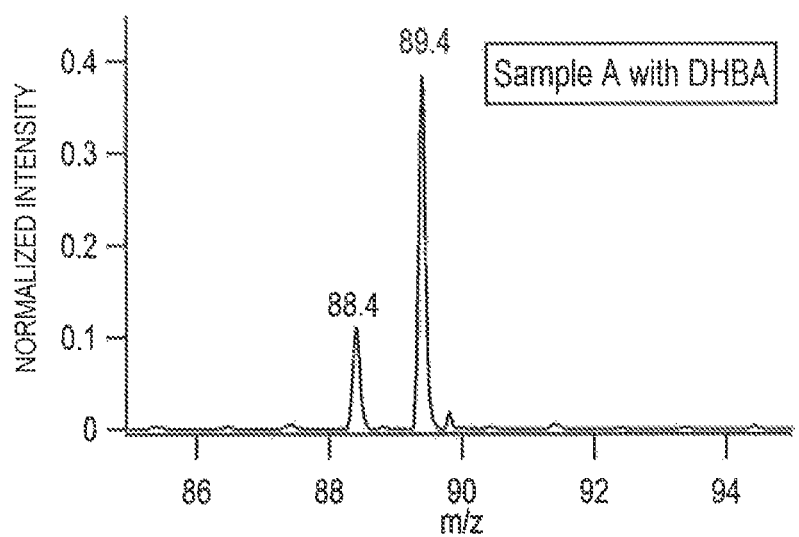
FIG. 26 Graphs showing mass spectrometry results for a sample of which the discharge time is 20 minutes by means of matrix-assisted laser desorption ionization/time-of-flight mass spectrometry, wherein (a) shows measurement results in the positive mode and (b) shows measurement results in the negative mode.
Figure 26:
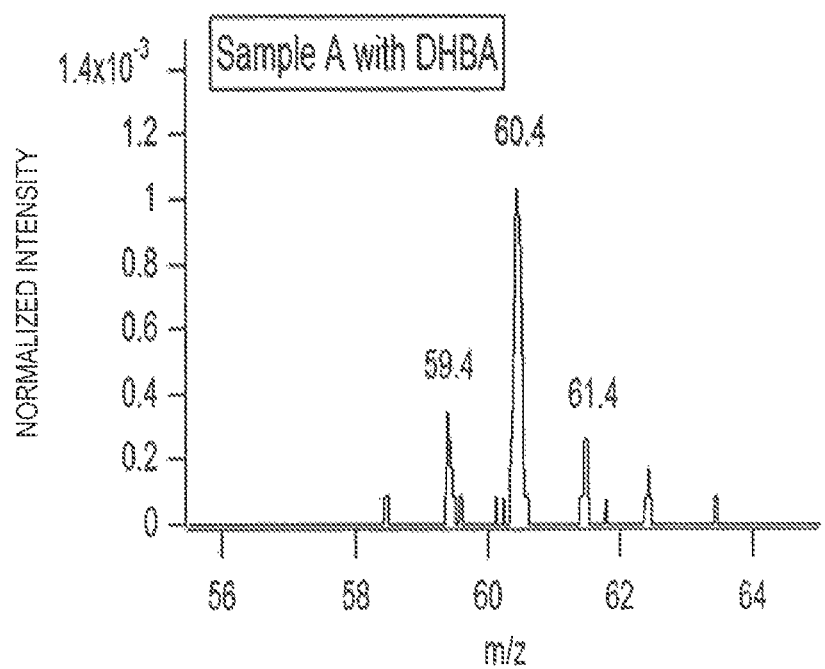

FIG. 25 shows results for a standard aqueous solution including performic acid, wherein FIG. 25(*a*) shows measurement results in the positive mode and FIG. 25(*b*) shows measurement results in the negative mode. FIG. 26 shows results for a sample of which the discharge time is 20 minutes, wherein FIG. 26(*a*) shows measurement results in the positive mode and FIG. 26(*b*) shows measurement results in the negative mode.

As a result, it is believed that the organic substance having an absorption at 191 nm is diformyl peroxide. The molecular weight of diformyl peroxide (HOC—O—O—COH) is M-90. It is not clear whether m/z=89.4 belongs to an ion having a molecular weight M=90 or to an ion of M-89 which has lost proton. It is believed that m/z=60.5 belongs to an ion whose mass is 61, m/z=60.5 to HOCOO—, m/z=59.5 to OCOO—, and m/z=61.5 to a parent molecular ion.

The reaction in which diformyl peroxide is generated is believed to be:

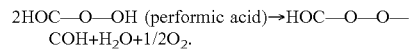

2HOC—O—OH (performic acid)→HOC—O—O—COH+H$_2$O+1/2O$_2$.

Figure 27:
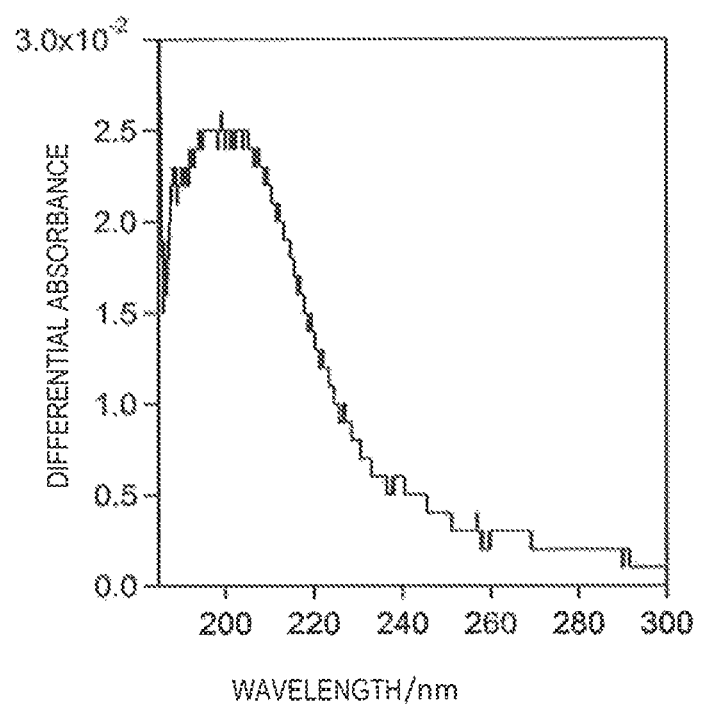
FIG. 27 A graph showing the difference spectrum between the UV spectrum of a sample of which the discharge time is 1 minute and the UV spectrum of a sample of which the discharge time is 20 minutes.

Next, the amount of performic acid generated was estimated. FIG. 27 shows the difference spectrum between the UV spectrum of a sample of which the discharge time is 1 minute and the UV spectrum of a sample of which the discharge time is 20 minutes.

The difference spectrum of FIG. 27 substantially matches the UV spectrum of performic acid. Therefore, the amount of performic acid generated was estimated, assuming that this difference spectrum belongs to performic acid generated over 19 minutes.

The absorbance at absorption maximum in the difference spectrum of FIG. 27 is 0.025, and assuming that the molar extinction coefficient of performic acid is 50, the concentration of performic acid in 500 ml is 0.5 mM, and the absolute value of performic acid generated over 19 minutes can be estimated to be 0.25 mmol. Converting this to the amount of generation over 1 minute gives 0.013 mmol. Since the electric power supplied is about 20 W, it means 1.2 kJ per 1 minute. Then, the energy efficiency is 0.011 mmol/kJ.

Figure 28:
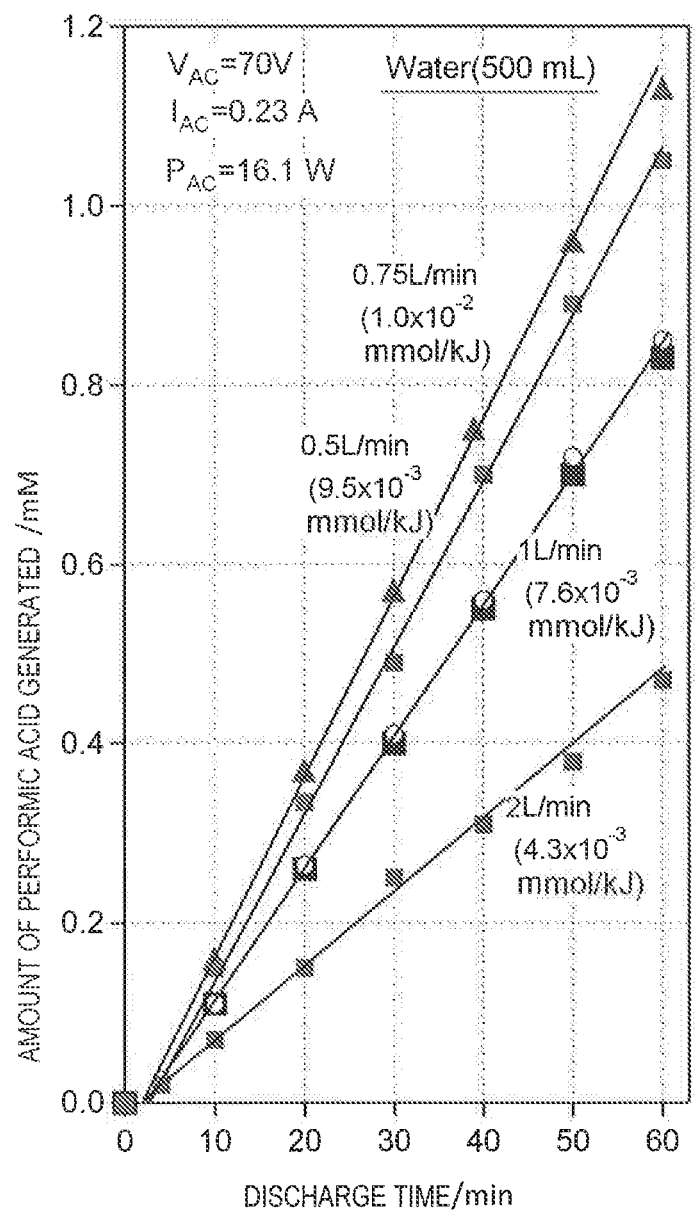
FIG. 28 A graph showing the relationship between the amount of performic acid generated and the flow rate of a carbon dioxide gas.
Figure 29:
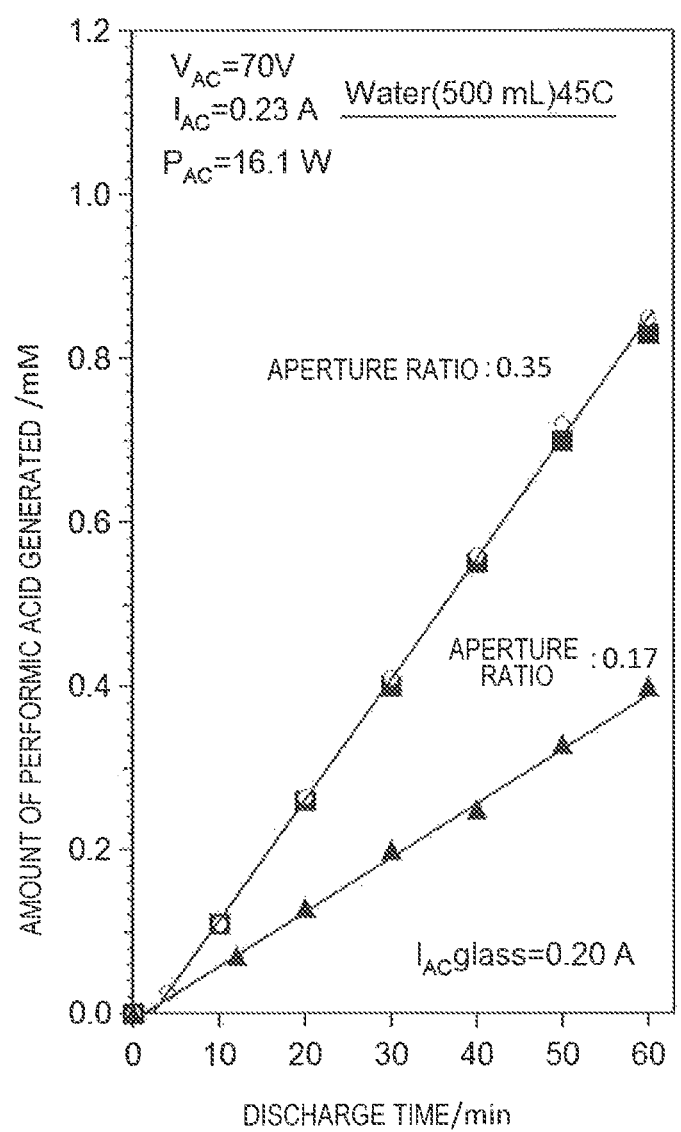
FIG. 29 A graph showing the relationship between the amount of performic acid generated and the aperture ratio of through holes in the electrode.

Referring to FIG. 28 and FIG. 29, the relationship between the amount of performic acid generated and the flow rate of the carbon dioxide gas and the aperture ratio of the through holes in the electrode will be described. The submerged discharge plasma device 1000 shown in FIG. 4 was used as described above in the experiment.

From the graph of FIG. 28 showing the relationship between the amount of performic acid generated and the flow rate of the carbon dioxide gas, it can be seen that the amount of performic acid generated increases as the flow rate of the carbon dioxide gas is increased if the flow rate of the carbon dioxide gas is between at least 0.5 L/min to 0.75 L/min, but amount of performic acid generated rather decreases if the flow rate is increased to at least 1 L/min or more. That is it can be seen that there is a preferable range for the flow rate of the carbon dioxide gas depending on the aperture ratio of the through holes in the electrode. In this case, the aperture ratio refers to the ratio of the total cross section of through holes effectively connecting the gas phase surface with the liquid phase surface with respect to the discharge area. That is, any through hole serving as an escaping hole for the gas are not included as an aperture.

From the graph of FIG. 29 showing the relationship between the amount of performic acid generated and the aperture ratio of the through holes in the electrode, it can be seen that the amount of performic acid generated decreases generally in proportion with the aperture ratio if the aperture ratio is smaller than the aperture ratio, 0.35, of the through holes 202 in the second electrode 200 of the submerged discharge plasma device 1000 shown in FIG. 4. Thus, it can be said that for the amount of performic acid generated, higher aperture ratios are preferable.

As described above, it was possible to synthesize an organic substance by means of a submerged discharge plasma from only carbon dioxide and water. Using this synthesis process, it is possible to immobilize carbon dioxide, which is said to be responsible for global warming. This also can be a promising method for synthesizing performic acid, as no methods have yet to be found for synthesizing pure performic acid. Performic acid, being very oxidative, is used cutting the disulfide bond in proteins. In organic synthesis, it is also used for oxidation reactions such as epoxidation and hydroxylation. In medicine and food industry, its sterilizing power is utilized.

INDUSTRIAL APPLICABILITY

The submerged plasma device according to the embodiment of the present invention can be used for subjecting a reaction product produced by a non-equilibrium plasma to a chemical reaction in order to newly synthesize, alter or decompose a substance. The submerged plasma device is characterized in that a plasma produced is adjacent to the substance to be treated by the plasma. Specifically, the submerged plasma device according to the embodiment of the present invention can be used for a sterilization process in a water purification/distribution plant, a drinking water, food plant, a semiconductor plant, a liquid crystal plant, a fish farm tank, an aquarium, etc. It can also be used for decomposing an organic substance during contaminated water treatment, for treating an industrial waste liquid, and for synthesizing a material in a solution.

Note that the electrode structure of the submerged plasma device according to the embodiment of the present invention can also be used in an in-gas plasma treatment. Examples include remote plasma CVD and remote plasma surface treatment, where the plasma region and the reaction region are separated from each other. Such an electrode structure can also be used as an air cleaner for decomposing contaminants in the atmospheric air.

With the submerged plasma device according to the embodiment of the present invention, it is possible to reduce the power supply capacity required for the operation thereof and to reduce the size and the weight thereof. This makes it easier to accommodate treatments in a local space. This also makes it easier to construct a treatment system based on the amount or treatment and the environment. This makes it possible to utilize the submerged plasma technique as a consumer appliance.

REFERENCE SIGNS LIST

100 First electrode
112 Solid dielectric layer
114 Inner space
116 Discharge chamber
118 Pipe
120 Gas introducing device
200 Second electrode
200a Liquid phase surface
200b Gas phase surface
202 Through hole
204 Contract surface
300 Liquid tank
302 Liquid
304 Liquid surface
400 Electrical circuit
402 First electrical conductor
404 Second electrical conductor
1000 Submerged plasma device

The invention claimed is:

1. An organic substance synthesis method using a submerged plasma device comprising:
    forming a plasma through discharge in a gas containing a carbon dioxide gas in contact with water; and
    generating an organic substance including performic acid or diformyl peroxide in the water by contact between the plasma and the water, wherein
    the submerged plasma device including:
    a first electrode;
    a solid dielectric layer in contact with the first electrode;
    a discharge chamber having an inner space accommodating the first electrode and the solid dielectric layer; and
    a second electrode formed by a metal and arranged so as to oppose the first electrode with the solid dielectric layer therebetween and so as to separate the inner space of the discharge chamber from water, the second electrode having a gas phase surface located on a side of the inner space and a liquid phase surface located on a side of the water, and the second electrode having a plurality of through holes connecting together the gas phase surface and the liquid phase surface, and wherein
    the organic substance is generated in the water through discharge in the gas including the carbon dioxide gas while forming an interface between the carbon dioxide gas and the water inside each of the through holes of the second electrode.

2. The organic substance synthesis method according to claim 1, wherein the discharge is dielectric barrier discharge.

3. The organic substance synthesis method according to claim 1, wherein the organic substance includes performic acid.

4. The organic substance synthesis method according to claim 2, wherein the organic substance includes performic acid.

* * * * *